United States Patent [19]

McCarthy

[11] 4,345,974

[45] Aug. 24, 1982

[54] SOLAR PROCESS

[76] Inventor: Walton W. McCarthy, Box 1091, Bozeman, Mont. 59715

[21] Appl. No.: 187,348

[22] Filed: Sep. 15, 1980

[51] Int. Cl.$^3$ .............................................. B01D 3/02
[52] U.S. Cl. ...................................... 203/19; 202/83; 202/234; 203/DIG. 1; 203/DIG. 13
[58] Field of Search .................. 99/278; 195/132, 133, 195/138, 139; 202/234, 83; 203/19, DIG. 1, DIG. 13

[56] References Cited

U.S. PATENT DOCUMENTS

| | | | |
|---|---|---|---|
| 102,633 | 5/1870 | Wheeler et al. | 202/234 |
| 3,299,589 | 1/1967 | Hay | 203/DIG. 1 |

*Primary Examiner*—Frank Sever
*Attorney, Agent, or Firm*—Arthur L. Urban

[57] ABSTRACT

Solar apparatus for producing alcohol including a fermentation section and a distillation section; the fermentation section including a shallow pan with a large top opening inclined at an angle to the horizontal, a transparent sealing member disposed over the top opening of the fermentation pan, a cover for the fermentation pan; mechanism for introducing fermentable material into the fermentation pan, mechanism for removing liquid from the fermentation pan, solar heating mechanism for the liquid, mechanism for transferring the heated liquid to the distillation pan; the distillation section including a shallow pan with a large top opening inclined at an angle to the horizontal, the distillation pan including a bottom section with a plurality of spaced rib members, the rib members being disposed in a substantially horizontal, parallel orientation, a transparent sealing member disposed over the top opening of the distillation pan, mechanism for selectively reducing the solar exposure of the distillation pan, liquid collecting structure disposed adjacent the lower edge of the distillation pan; and mechanism for controlling the temperatures of the fermentable material disposed within the fermentation pan and the distillation pan.

A solar process for producing alcohol including the steps of preparing an aqueous mixture including fermentable material, exposing the aqueous fermentable mixture to solar radiation to heat the mixture to an elevated temperature between about 80° and 100° F., maintaining the aqueous fermentable mixture at the elevated temperature for a time sufficient to ferment substantially all of the fermentable material, separating the liquid from the fermented mixture, exposing the fermented liquid to solar radiation to heat the liquid to a temperature approaching the boiling point of the alcohol, passing the heated liquid continuously in small quantities over an inclined ribbed surface in an enclosed chamber while subjecting the liquid to solar radiation, vaporizing the alcohol component of the liquid, condensing the vaporized alcohol component on the under side of an inclined surface disposed above but closely adjacent to the inclined ribbed surface, and collecting the condensed alcohol adjacent the lower edge of the inclined condensing surface.

2 Claims, 5 Drawing Figures

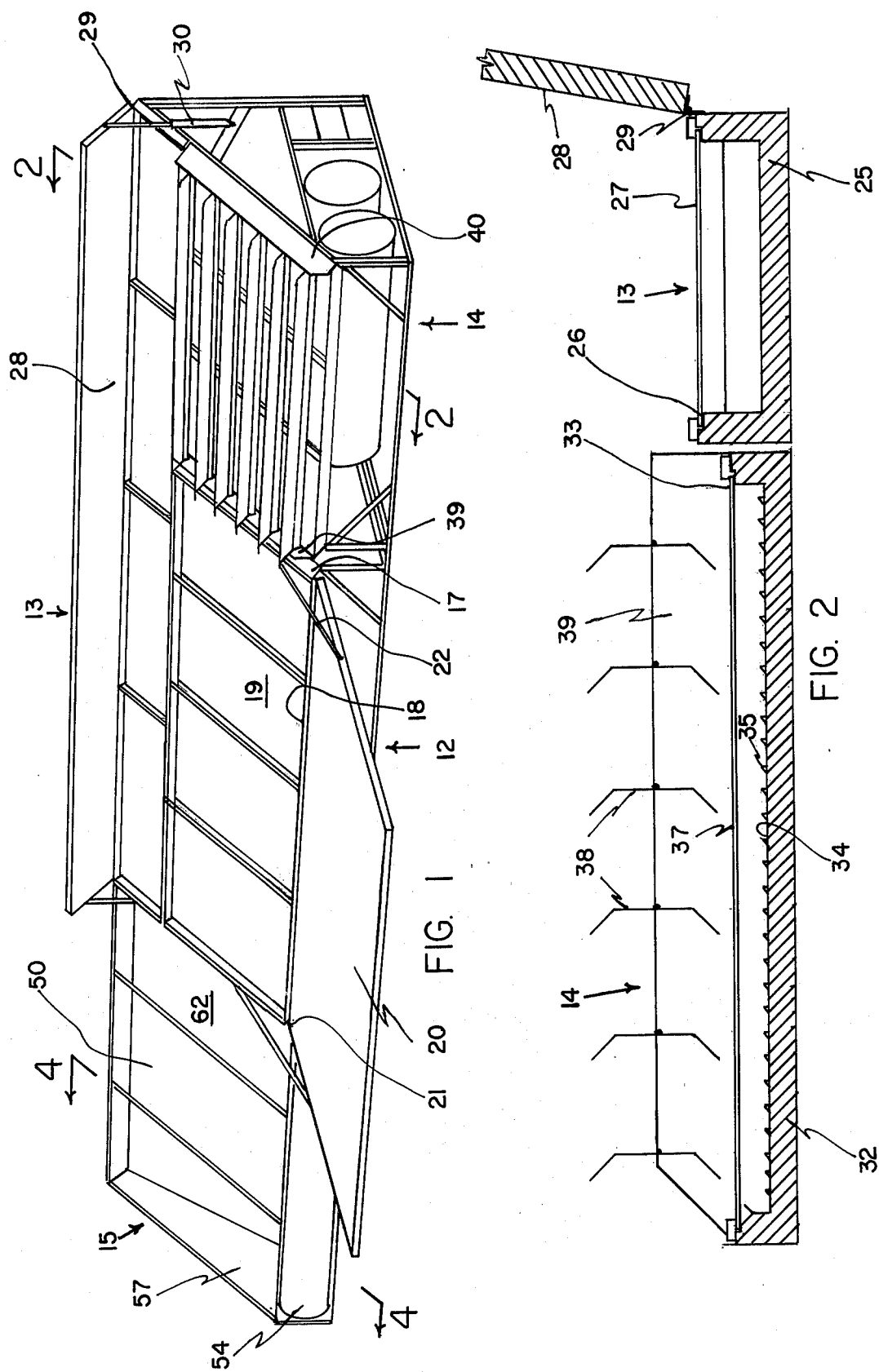

SOLAR PROCESS

This invention relates to a novel solar apparatus and process and more particularly relates to a new solar apparatus and process for producing alcohol.

Alcohol and similar products have been produced by a variety of methods through the years. Ordinarily, alcohol is produced by fermenting an organic material such as grain or another plant derivative. This may be accomplished, for example, by allowing the organic material to decay or ferment naturally or by the application of heat. After fermentation, the solid material is separated from the liquid which is primarily a mixture of water and alcohol. The alcohol is separated from the mixture by distillation. The mixture is heated until one of the components is vaporized or boiled from the mixture. The vapors are condensed on a cool surface and the condensed liquid collected.

Heating of the fermentable material generally is done by using conventional fossil fuels such as oil, natural gas, coal and the like. With the large increases in the cost of such fuels in recent years, the cost of alcohol has increased drastically. The price increases of most alcoholic products such as alcoholic beverages, medicines and the like have been accepted by the public because their costs do not represent a significant proportion of a family's budget.

However, the recent increases in the cost of fossil fuels has greatly increased interest in alcohol as a fuel source. One of the principal areas of interest is the blending of alcohol with gasoline to form a product called "gasohol". Gasohol which usually comprises about 10% alcohol and 90% gasoline can be used in place of straight gasoline in internal combustion engines without changing the engine.

One of the problems with gasohol is its high cost. Although alcohol is more costly to produce than gasoline, interest in gasohol continues because it provides a way of reducing the dependency of the United States on imported oil. Thus, the U.S. government currently is subsidizing the production of alcohol for gasohol. In spite of the subsidy, there is a general uneasiness about increasing the use of gasohol because of concern that the subsidy may be withdrawn. Thus, there has been limited investment in commercial alcohol plants for gasohol.

In view of the large supplies of fermentable materials such as grains in the United States and the ever increasing cost of imported petroleum, there continues to be considerable effort directed to finding less expensive ways to produce alcohol. In spite of these efforts, there still remain major deterrents to the success, that is, the cost of the raw material and the energy requirements for producing alcohol.

The present invention provides a novel apparatus and process for producing alcohol. The apparatus and process of the invention produce alcohol at less cost than previously known procedures. The apparatus and process utilize solar energy in a unique way to produce alcohol.

The apparatus and process of the present invention are relatively simple to use. The apparatus can be installed by an ordinary homeowner or farmer with a minimum of instruction. The process of the invention can be carried out by a layman without special knowledge or skills.

The apparatus of the invention is simple in design and can be fabricated from commercially available components and materials. The apparatus can be manufactured relatively inexpensively. The apparatus can be transported conveniently on a flat bed truck and requires a minimum of installation on the site. The apparatus has a long useful life and requires little maintenance.

Other benefits and advantages of the novel solar apparatus and process of the present invention will be apparent from the following description and the accompanying drawings in which:

FIG. 1 is a view in perspective of one form of the solar apparatus of the invention for producing alcohol;

FIG. 2 is an enlarged sectional view of the solar apparatus taken along line 2—2 of FIG. 1;

Figure 3:
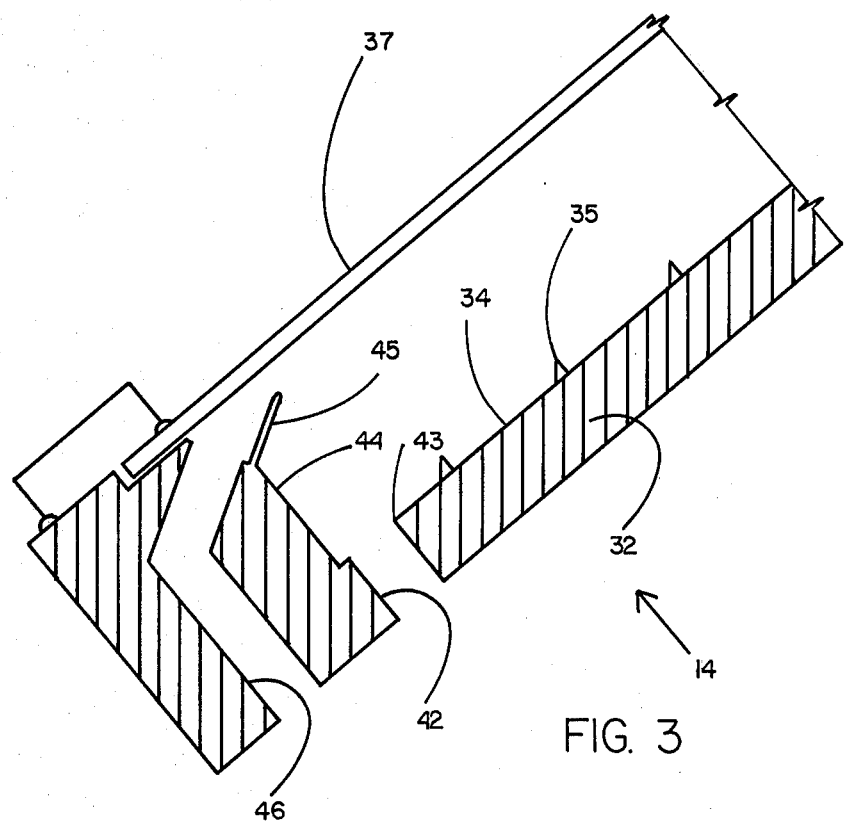
FIG. 3 is a greatly enlarged fragmentary sectional view of the lower portion of the distillation section of the solar apparatus.
Figure 4:
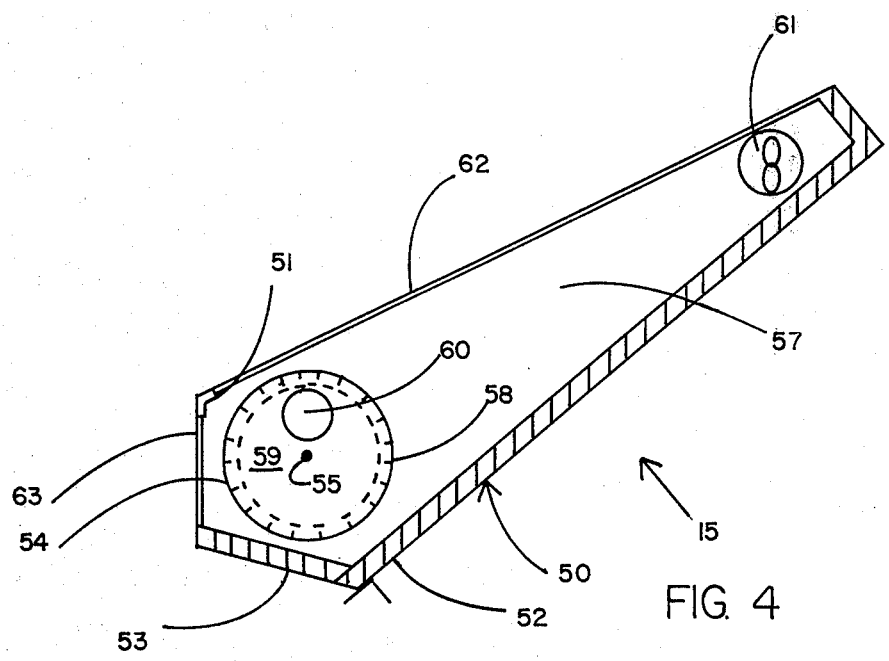
FIG. 4 is an enlarged sectional view of the solar apparatus taken along line 4—4 of FIG. 1.

As shown in FIGS. 1-4 of the drawings, one form of the novel solar apparatus for producing alcohol of the present invention includes a fermentation section 12, a heating section 13 and a distillation section 14. Advantageously, as shown, the apparatus also includes a dryer section 15.

The fermentation section 12 includes a shallow pan 17 with a large top opening 18 inclined at an angle to the horizontal. The fermentation section 12 also includes a transparent member 19 disposed over the top opening 18 of the pan 17. Means are provided for covering the transparent member 19 such as cover 20 which is pivotally connected to one edge of fermentation pan 17 through hinges 21. A piston and cylinder combination 22 moves the cover 20 from a closed position adjacent transparent member 19 to an open position remote therefrom.

Heating section 13, as shown in section in FIG. 2, is similar in structure to fermentation section 12 and includes a shallow pan 25 with a large top opening 26. The heating section 13 advantageously is inclined at an angle to the horizontal similar to fermentation section 12. Top opening 26 has a transparent member 27 disposed thereover. Means shown as cover 28 is pivotally connected to the top edge of the heating pan 25 through hinges 29. A piston and cylinder combination 30 moves the cover 28 from an open to a closed position adjacent the transparent member 27.

Distillation section 14 includes a shallow pan 32 with a large top opening 33 inclined at an angle to the horizontal. Pan 32 includes a bottom section or panel 34 with a plurality of spaced rib members 35 (shown in FIGS. 2 and 3). The rib members 35 are disposed in a generally horizontal, parallel orientation. A transparent sealing member 37 is disposed over top opening 33 of pan 32.

Means are provided for selectively reducing or changing the solar exposure of the transparent sealing member 37. As shown, such means may include a plurality of shutter sections 38 pivotally mounted on end supports 39 and 40. Actuating means (not shown) are provided to effect coordinated movement of the shutters.

Liquid collecting means are disposed adjacent the lower edge of the distillation pan 32. As shown in FIG. 3, a passage 42 is located along the bottom edge 43 of bottom section 34. Adjacent passage 42 is located a deflector section 44 with an extension 45. The free edge of extension 45 is disposed closely adjacent to but spaced from the lower surface of transparent sealing member 37. A second passage 46 extends from the side of extension 45 opposite to passage 42.

Drying section 15 shown as located adjacent to fermentation section 12 includes pan 50 with a large top opening 51 inclined at an angle to the horizontal. Pan 50 has an inclined bottom section including a long portion 52 and a short portion 53 extending at an angle therefrom to form a trough configuration. A rotatable drying cylinder 54 is positioned in the lower part of the drying section 15 above the trough. Cylinder 54 is rotatably supported on a shaft 55 carried by dryer end panels, one of which 57 is shown. Cylinder 54 has an outer surface with perforations 58. Drying cylinder 54 has end sections, one of which section 59 has an opening 60. Opening 60 is disposed toward one side of the end section 59. A fan 61 is located adjacent the upper edge of dryer pan 50. The drying pan 50 is enclosed with transparent members 62 and 63.

Figure 5:
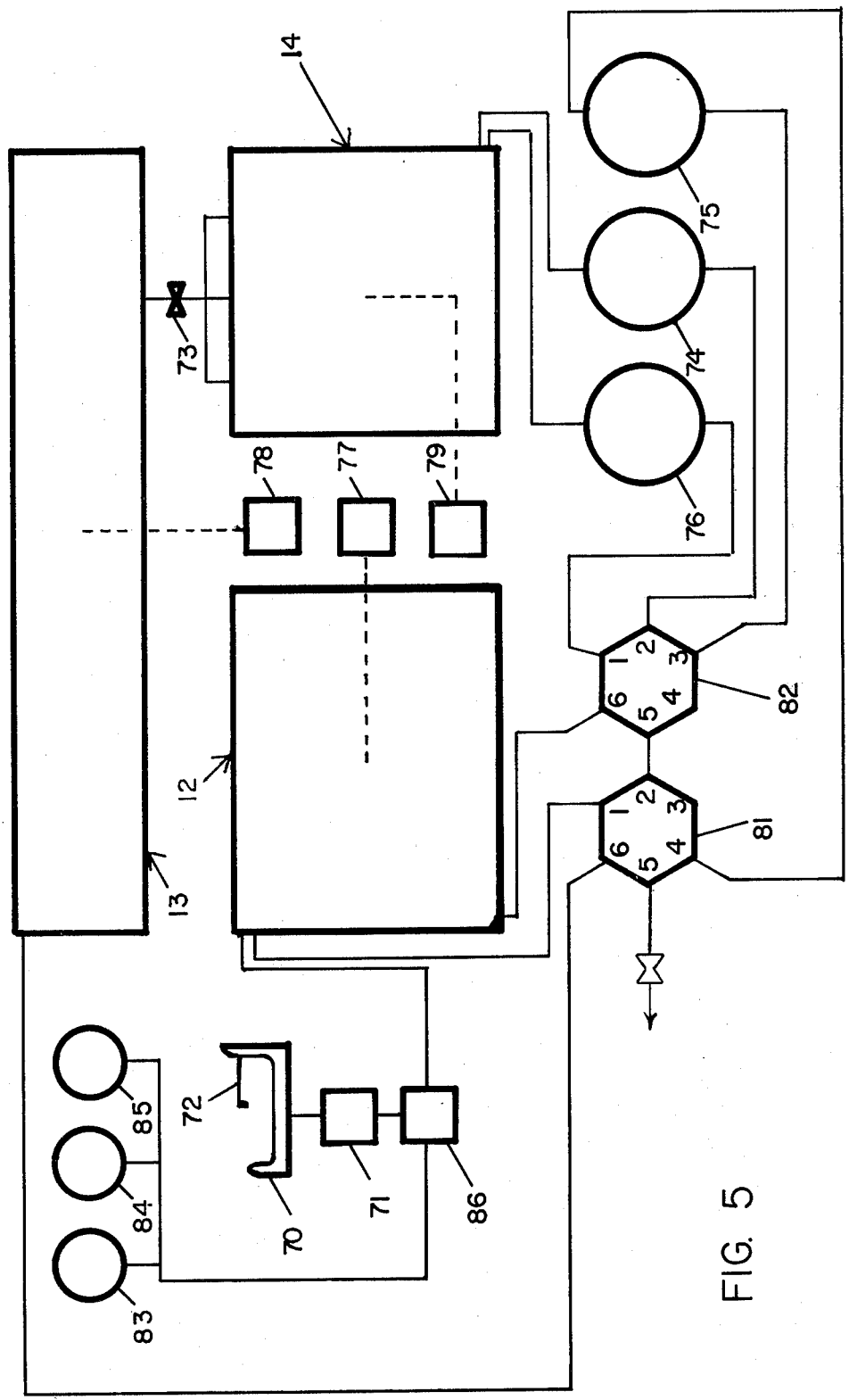
FIG. 5 is a schematic flow diagram of the process of the invention for producing alcohol.

The solar process for producing alcohol in accordance with the present invention as illustrated particularly in FIG. 5 includes the steps of preparing an aqueous mixture of the fermentable material to be employed. The fermentable material may be any of a variety of plant materials such as grains, vegetables, greens, as well as sugar beets, potatoes, comfrey and the like. In the case of materials with a hard shell and/or large size, it may be desirable to crush or pulverize the materials.

The fermentable material advantageously is vigorously mixed with water prior to fermentation to provide a uniform mixture. Where the process is conducted on a relatively small scale, the aqueous mixture may be formed by feeding the material into a sink 70 with a garbage disposal type of mixer 71 which operates with a continuous flow of water 72. The pH of the mixture in section 12 advantageously is adjusted if necessary with an acid or base to a pH between about 4 and 5 and preferably about 4.5.

The mixture is transferred to fermentation section 12 and heated by solar radiation to an elevated temperature, for example, between about 80° and 100° F. and preferably about 90° F. Then, the cover 20 on section 12 is closed. Yeast or another fermentation initiating agent is added to the heated mixture. The mixture is permitted to remain in the fermentation section 12 at 90° F. for about two days to substantially complete the fermentation process. Thereafter, the liquid is drawn from the section 12 and transferred to heating section 13. The solids remaining are transferred to dryer section 15 (FIG. 1) and processed as will be described hereafter.

The liquid in heating section 13 is heated to a temperature of about 180° F. by opening the cover 28 and exposing the liquid to solar radiation. When the liquid has attained a temperature of about 180° F., thermostatically controlled valve 73 permits liquid to flow into distillation section 14.

The heated liquid enters the top of the inclined distillation section 14 and flows downwardly over the ribbed bottom surface 34 of the distillation pan. The ribs 35 tend to temporarily trap or hold back the liquid as it flows downwardly. The temperature of the liquid on the ribbed surface 34 is maintained at about 180° F. by solar radiation. The heating is controlled by adjusting shutters 38 through suitable automatic thermostatic controls (not shown).

As the thin film of liquid flows downwardly over the ribbed surface 34, the alcohol component of the liquid evaporates. The alcohol vapor condenses on the under surface of transparent sealing member 37 and runs down the surface to the bottom edge and into passage 46. The water rich portion of the liquid runs down the ribbed bottom surface 34 and into passage 42.

The alcohol collecting in tank 74 is tested for proof or alcohol concentration. This can be done with a hydrometer or other suitable instrument. If the alcohol tests at more than 170 proof or the value desired, the alcohol can be transferred to an appropriate storage tank 75 for subsequent use. Should the alcohol contain too much water, that is, less than about 170 proof, the alcohol component can be transferred back to the heating section 13 and after being heated to about 180° F. is passed downwardly through the distillation section 14 to remove more of the water from the alcohol fraction.

The water fraction from passage 42 which is collected in tank 76, may contain some fermentable sugar. The water fraction can be transferred back to the fermentation section 12 and mixed with additional quantities of fermentable material for fermentation again.

Control of the solar process of the invention may be achieved through expedients such as heat sensors 77, 78 and 79 for fermentation section 12, heating section 13 and distillation section 14, respectively. Also, valves 81 and 82 may be utilized to transfer the various liquids employed or generated in the process from one section to another as desired or required. The additives employed in the process may be stored in tanks 83, 84, 85, etc. and added through pump 86 associated with mixer 71.

The solid material from the fermentation section 12 is added to drying cylinder 54 of drying section 15. The drying cylinder 54 is rotated on shaft 55 by suitable drive means such as a motor (not shown). At the same time, fan 61 circulates air heated by solar radiation within the drying section through the perforations 58 of cylinder 54 and thus through the wet solid material tumbling therein. The rotation of the cylinder 54 and the air circulation of the fan are continued until the excess moisture in the solid material has been evaporated. The dried solid material then is removed from the cylinder 54 through opening 60. The dried material may be used for a number of uses such as animal feed, soil conditioners and the like.

The above description and the accompanying drawings show that the present invention provides a novel apparatus and a novel process for producing alcohol at less cost than previous procedures. The process and apparatus produce alcohol through a unique utilization of solar energy.

The apparatus and process of the present invention can be installed easily by a homeowner or farmer after only a minimum of instruction. The apparatus and process are relatively simple to use. The process can be conducted by a layman without special knowledge or skills.

The apparatus of the invention is simple in design and can be manufactured relatively inexpensively. The apparatus can be fabricated from commercially available components and materials using industrial fabricating techniques and semi-skilled labor.

The apparatus can be transported conveniently to the installation site on a flat bed truck. The apparatus of the invention requires a minimum of erection and installation on the site before operation can be started. The apparatus is durable in construction and has a long useful life. The apparatus requires little maintenance.

It will be apparent that various modifications can be made in the particular solar apparatus and process of the invention described in detail and shown in the drawings within the scope of the invention. The size, configuration and arrangement of components can be changed to meet specific requirements. Also, the fermentable material selected can utilize materials that are readily available locally at relatively low cost. In addition, the transfer of materials through the apparatus and process can be effected in other ways. Therefore, the scope of the present invention is to be limited only by the following claims.

What is claimed is:

1. A solar process for producing alcohol including providing an apparatus of a size sufficiently small to be conveniently carried on a flat bed truck, said apparatus including a fermentation section and a distillation section; said fermentation section including a shallow pan with a large top opening inclined at an angle to the horizontal, a transparent member disposed over said top opening of said fermentation pan, cover means for said fermentation pan; means for introducing fermentable material into said fermentation pan, means for removing liquid from said fermentation pan, solar heating means for said liquid, means for transferring said heated liquid to said distillation section; said distillation section including a shallow pan with a large top opening inclined at an angle to the horizontal, said distillation pan including a bottom section with a plurality of spaced rib members, said rib members being disposed in a substantially horizontal, parallel orientation, a transparent member disposed over said top opening of said distillation pan, means for selectively reducing the solar exposure of said distillation pan, liquid collecting means disposed adjacent the lower edge of said distillation pan; and means for controlling the temperatures within said fermentation pan and said distillation pan; said process also including the steps of preparing a pulverized fermentable material, vigorously mixing water with said pulverized fermentable material to form a uniform aqueous mixture including said fermentable material, adjusting the pH of said mixture to between about 4 and 5, selectively exposing said aqueous fermentable mixture to solar radiation in said fermentation section to heat said mixture to an elevated temperature between about 80° and 100° F., maintaining said aqueous fermentable mixture at said elevated temperature for a time sufficient to ferment substantially all of said fermentable material, separating liquid from said fermented mixture, exposing said fermented liquid to solar radiation in said distillation section to heat said liquid to a temperature approaching the boiling point of said alcohol between about 170° and 190° F., passing said heated liquid continuously in small quantities over said inclined rib members while subjecting said liquid to solar radiation through said transparent member of said distillation pan, vaporizing the alcohol component of said liquid, controlling the exposure of said fermented liquid to solar radiation during said vaporizing step, condensing said vaporized alcohol component on the under side of said transparent member disposed closely above said inclined rib members, and collecting said condensed alcohol component.

2. A solar process according to claim 1 including exposing said separated solid fermented material to solar radiation to evaporate moisture therefrom.

* * * * *